United States Patent [19]

Bousquet et al.

[11] 4,174,448
[45] Nov. 13, 1979

[54] PROCESS FOR THE PREPARATION OF THIENOPYRIDINE DERIVATIVES

[75] Inventors: André Bousquet, Portet; Emile Braye, Lagardelle, both of France

[73] Assignee: Parcor, Paris, France

[21] Appl. No.: 913,073

[22] Filed: Jun. 6, 1978

[30] Foreign Application Priority Data

Jul. 12, 1977 [FR] France ................................. 77 21517

[51] Int. Cl.² .......................................... C07D 495/04
[52] U.S. Cl. ..................................... 546/114; 424/256
[58] Field of Search ................... 260/294.8 C; 546/114

[56] References Cited

U.S. PATENT DOCUMENTS

| 4,051,141 | 9/1977 | Castaigne | 546/114 |
| 4,065,460 | 12/1977 | Heymes et al. | 546/114 |
| 4,075,340 | 2/1978 | Maffrand | 424/256 |
| 4,076,819 | 2/1978 | Maffrand | 424/256 |

Primary Examiner—Alan L. Rotman
Attorney, Agent, or Firm—Young & Thompson

[57] ABSTRACT

This invention relates to a process for the preparation of compounds having the general formula:

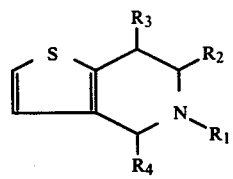

(I)

in which: $R_1$ represents a hydrogen atom, an optionaly substituted alkyl, aryl or aralkyl radical; $R_2$ and $R_3$ are the same or different and represent independently a hydrogen atom, a lower alkyl, aryl or heterocyclic radical; and $R_4$ represents a hydrogen atom or an alkyl, cycloalkyl, alkoxy carbonyl, carboxy, aryl or heterocyclic radical, comprising reacting a compound having the formula:

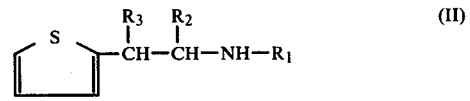

(II)

in which $R_1$, $R_2$ and $R_3$ are as defined above, with a compound having the formula:

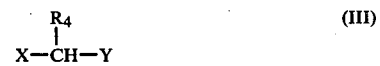

(III)

in which $R_4$ is as defined above; X is a halogen atom, or an optionally substituted alkoxy, thioalkyl or amino group; and Y represents an optionally substituted alkoxy, thioalkyl or amino group, or a group of the formula:

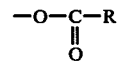

in which R is a lower alkyl or aryl radical; or both the groups X and Y, together with the carbon atom to which they are attached, form a 6-membered hexahydro-S-triazinic, trioxannic or trithianic heterocyclic nucleus, in an inert solvent, at a temperature between 0° and 150° C. and in an anhydrous medium, and, if desired, liberating the free base.

7 Claims, No Drawings

PROCESS FOR THE PREPARATION OF THIENOPYRIDINE DERIVATIVES

This invention relates to a process for the preparation of thienopyridine derivatives.

In U.S. Pat. No. 4,127,580 is described a process for the preparation of thienopyridine by reaction of an optionally substituted 2-$\beta$-thienyl-ethylamine with formaldehyde in the presence of an acid. Said reaction is preferably effected in two steps, first by reacting $\beta$-thienylethylamine with formaldehyde, and then by cyclization of the resulting material in anhydrous medium, with an anhydrous acid. However, the rate of conversion of the starting material is only of the order of 60-65%, which necessitates a recycling of the unreacted starting material. The utility of such thienopyridines was also disclosed in the above-identified patent, namely, anti-inflammatory, vasodilatator and blood platelet aggregation inhibitor action; and a process for their preparation was also disclosed in U.S. Pat. No. 4,051,141, Sept. 27, 1977, which was a streamlined division of Ser. No. 435,036, filed Jan. 21, 1974, which in turn corresponded to French application Ser. No. 73 03503, filed Feb. 1, 1973.

In addition, said process does not permit the preparation of thienopyridine substituted at 4-position by means of the Pictet Spengler reaction, by action of an aldehyde on a thienylethylamine derivative.

It is also known to prepare 1,2,3,4-tetrahydroisoquinolines from N-benzoyl derivatives of beta-arylamine and chloromethylmethylether, as disclosed in Chemical Communications, 1969, 1283-4. It shoud be noted, however, that cyclization occurs on a highly activated benzene nucleus and that the reaction site is an amide.

The purpose of the present invention is to overcome said drawbacks by providing a process which makes it possible both to obtain derivatives substituted at 4-position and to obtain markedly higher yields and conversion rates.

Thus, this invention relates to a process for the preparation of compounds having the general formula:

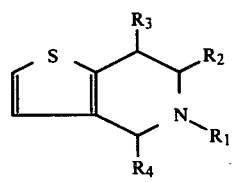

in which: $R_1$ represents a hydrogen atom, an optionally substituted alkyl, aryl or aralkyl radical; $R_2$ and $R_3$ are the same or different and represent independently a hydrogen atom, a lower alkyl, aryl or heterocyclic radical; and $R_4$ represents a hydrogen atom or an alkyl, cycloalkyl, alkoxy carbonyl, carboxy, aryl or heterocyclic radical, comprising reacting a compound having the formula:

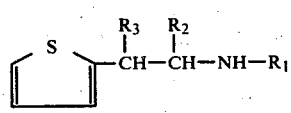

in which $R_1$, $R_2$ and $R_3$ are as defined above, with a compound having the formula:

in which $R_4$ is as defined above; X is a halogen atom, or an optionally substituted alkoxy, thioalkyl or amino group; and Y represents an optionally substituted alkoxy, thioalkyl or amino group, or a group of the formula:

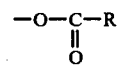

in which R is a lower alkyl or aryl radical; or both the groups X and Y, together with the carbon atom to which they are attached, form a 6-membered hexahydro-S-triazinic, trioxannic or trithianic heterocyclic nucleus, in an inert solvent, at a temperature between 0° and 150° C. and in an anhydrous medium, and, if desired, liberating the free base.

The compounds of the formula (III) which are used in the process according to this invention may be illustrated by the following compounds, depending on the nature of X and Y:

(a) a halogenomethyl ether of the type

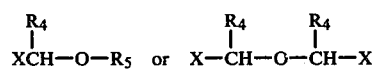

in which X is a halogen atom such as Cl or Br and $R_5$ is a lower alkyl or aryl radical;

(b) a halogenomethyl thio ether of the type

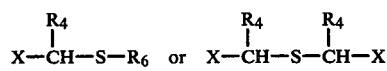

in which X is a halogen atom such as Cl or Br and $R_6$ is a lower alkyl or aryl radical;

(c) a halogenomethyl ester of the type

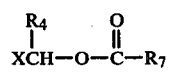

in which X is a halogen atom such as Cl or Br and $R_7$ is a lower alkyl or aryl radical;

(d) a S-hexahydro-S-triazine having the formula:

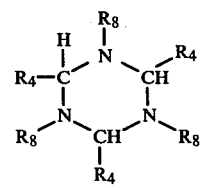

or an amino derivative having the formula:

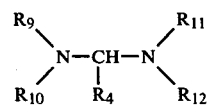

in which formulae $R_8$, $R_9$, $R_{10}$, $R_{11}$ and $R_{12}$ are lower alkyl radicals which may, between them, form a nitrogen bridge, or the same or different aryl radicals;

(e) a trioxan having the formula:

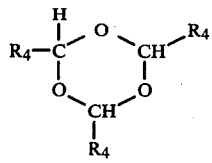

or a polyoxymethylene derivative having the formula

in which $R_{13}$ and $R_{14}$ are hydrogen atoms or the same or different lower alkyl or aryl radicals, and $n \geq 1$;

(f) a trithian having the formula:

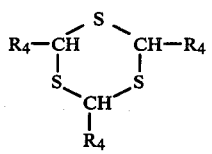

or a polythiomethylene derivative having the formula:

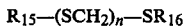

in which $R_{15}$ and $R_{16}$, which may be the same or different, are lower alkyl or aryl radicals and $n \geq 1$.

The reaction between the compound of the formula (II) and the compound of the formula (III) is conducted within an inert solvent at a temperature of 0°–150° C., but preferably between room temperature and the boiling point of the more volatile compound which is generally one of the solvents used.

This reaction occurs presumably via the formation of an intermediate compound which is not isolated, but cyclized in situ, as discussed hereinafter.

However, the cyclization of this intermediate compound requires the presence of an acid which is either generated in the medium by the reaction for the formation of the intermediate, or added when it is not provided by said reaction for the formation of the intermediate. The in situ formation of acid is dependent on the nature of the compound of the formula (III). Thus, for the compounds of the formula (III) of types a, b and c one notes the formation of such an acid of the formula XH which functions as cyclization agent, whereas no acid is formed in the case of the compounds of the formula (III) of types d, e and f.

In the latter case, use is made of a reaction solvent which contains an acid which may be, for example: an inorganic acid, which is preferably anhydrous, such as hydrochloric, sulfuric, hydrobromic and phosphoric acids; an organic carboxylic acid such as oxalic, acetic, monochloracetic acids, or a sulfonic acid such as methanesulfonic and benzenesulfonic acids.

In the cases where the acid is generated in the medium, it is preferred to add the compound of the formula (III) to the solution of the compound of the formula (II), although the reverse procedure is also possible. In the other cases, it is preferred to add a mixture of compounds of the formulae (II) and (III) to the reaction solvent containing the cyclization acid.

Most of the times, the reaction occurs rapidly; but it may sometimes be advantageous to apply external heating at the end of the reaction, to speed up same.

The reaction may be effected at atmospheric pressure or at superatmospheric pressure; but atmospheric pressure is generally sufficient.

The reaction is conducted within a solvent inert with respect to the reagents, particularly with respect to the compounds of the formula (III). Said solvent should be anhydrous, because water decomposes the compounds of the formula (III). It is preferred to use an aprotic solvent, which may be of polar nature, such as dimethylformamide, dimethylsulfoxide, hexamethyl phosphorotriamide or another solvent, such as benzene, toluene; a chlorinated solvent such as a chlorinated hydrocarbon; or light ethers.

It is advantageous to conduct the reaction within a solvent in which the halide of the compound of the formula (I) is scarcely —if at all—soluble because, indeed, it is then possible to isolate the salt of the compound of the formula (I), at the end of the reaction, by filtration of the resulting precipitate. In addition, this procedure provides excellent yields, in addition to convenient processing.

The compounds of the formulae (II) and (III) are reacted in stoichiometric amounts or, if desired, with an excess of compound of the formula (III) up to about 50%.

While not wishing to be bound by any reaction mechanism, Applicant thinks it should be said that the reaction occurs in two steps, which two steps are not distinct, practically:

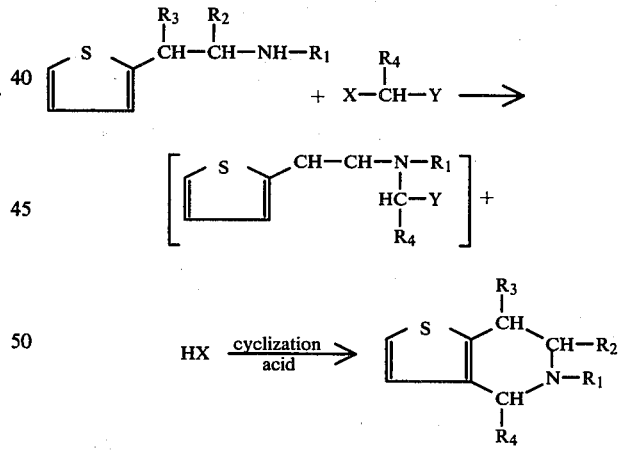

Thus, the cyclization occurs with formation of an alcohol, a mercaptan, an amine or water.

Said cyclization is obtained with very good yields and conversion rates of the starting material. Thus, in the cyclizations where the reagent is chloromethyl methyl ether, or chloromethyl methylthioether, the conversion rate of the compound of the formula (II) is close to 100% and the yields are of the order of 90–95%.

Also, by means of the process of this invention, it is possible to obtain thienopyridine derivatives in which the group $R_4$ is an aryl group such as the phenyl group, a heterocyclic group such as the 2-thienyl group, an aliphatic or cycloaliphatic radical or a functional group such as alkoxy-carbonyl, carboxy.

The preparation of the starting reagents of the formula (III) is readily effected by procedures known in the literature and which are outside the scope of this invention. Some compounds of the formula (III) are unstable and, therefore, they should be prepared just prior to use in the process of this invention in which they are used without further purification.

The following non-limiting Examples are given to illustrate the process of this invention.

EXAMPLE 1

Preparation of 5-(2-chloro-benzyl)-4,5,6,7-tetrahydrothieno[3,2-c]pyridine hydrochloride To a solution of 50.8 g (0.2 M) N-(2-chloro-benzyl)-2-(2-thienyl)-ethylamine in 70 ml dimethylformamide heated at 60° C. is added, over 7 minutes, 22.7 g (0.24 M) chloromethylmethylether. The temperature of the reaction medium is maintained at 60° C. throughout the addition step by cooling with water. Thirty minutes after completion of the chloromethylmethylether addition, the medium is cooled to 20° C. The desired product, which has precipitated out, is filtered and washed with 2×70 ml acetone, to give 45.1 g 5-(2-chloro-benzyl)-4,5,6,7-tetrahydro-thieno[3,2-c]pyridine hydrochloride (Yield: 75%).

Treatment of the filtrates produces another 9 g of the desired product (Yield: 90%. M.p.=190° C.).

EXAMPLE 2

Preparation of 5-(2-chloro-benzyl)-4-ethoxycarbonyl-4,5,6,7-tetrahydro-thieno[3,2-c]pyridine hydrochloride Into a three-necked 250 ml flask are added 25.1 g (0.1 M) N- (2-chloro-benzyl)-2-(2-thienyl)ethylamine dissolved in 30 ml dimethylformamide. Ethyl 2-chloro-2-ethoxy-acetate (18.3 g; 0.11 M) is then added over 6 minutes, and the resulting material is heated at 80° C. for 4 hours after which the desired product begins to precipitate out. After cooling of the medium, the product is filtered off and recrystallized from 3×20 ml acetone, to give 20.5 g 5-(2-chloro-benzyl)-4-ethoxy-carbonyl-4,5,6,7-tetrahydrothieno[3,2-c]pyridine hydrochloride (Yield: 55%).

Treatment of the filtrates provides another 10 g crude product (M.P.=156° C.). The crude product is obtained analytically pure by recrystallization from ethanol-isopropyl ether (Overall yield: 81.8%).

EXEMPLE 3

Preparation of 5-(2-chloro-benzyl)-4-(2-thienyl)-4,5,6,7-tetrahydro-thieno[3,2-c]pyridine hydrochloride (a) Preparation of (2-thienyl)chloromethylmethylether Into a stirred flask are added 112 g (1 M) (2-thienyl)-carboxaldehyde, 50 g (1.55 M) methanol, 125 ml methylene chloride and 150 g sodium sulfate. The reaction medium is cooled to −35° C. and a stream of dry gaseous hydrochloric acid is bubbled through to saturation while preventing the temperature from exceeding 20° C. After interruption of the bubbling of hydrochloric acid, the reaction medium is left at −20° C., with stirring, for 2 hours. The methylene chloride is then evaporated off at −20° C. to give the crude (2-thienyl)-chloromethylmethylether.

(b) Preparation of 5-(2-chloro-benzyl)-4-(2-thienyl)-4,5,6,7-tetrahydro-thieno[3,2-c]pyridine hydrochloride N-(2-chloro-benzyl)-2-(2-thienyl)ethylamine is reacted with the ether prepared in (a) above, in a manner analogous to that described in Example 1, to give the dersired compound (melting point of the base: 109° C.).

EXAMPLES 4 and 5

The following compounds are prepared in a manner analogous to that described in Example 1:

5-(2-chloro-benzyl)4-phenyl-4,5,6,7-tetrahydro-thieno[3,2-c]-pyridine hydrochloride (M.p. of the base: 95° C.)

5-(2-chloro-benzyl)-4-isopropyl-4,5,6,7-tetrahydro-thieno[3,2-c]-pyridine hydrochloride (M.p. of the base: 172° C.)

respectively, from N-(2-chloro-benzyl)-2-(2-thienyl-)ethylamine and the following compounds:
α-chlorobenzyl-methylether,
1-chloro-1-ethoxy-2-methyl-propane.

EXAMPLE 6

Preparation of 4,5,6,7-tetrahydro-thieno[3,2-c]pyridine hydrochloride

To a solution of 12.7 g (0.1 M) 2-(2-thienyl)ethylamine in 20 ml dimethylformamide heated at 55° C. are added, over 10 minutes, 8.05 g (0.1 M) chloromethylmethylether diluted in 10 ml dimethylformamide. After addition of the chloromethylmethylether, the medium is maintained at 70° C. for 2 hours, and is then cooled to room temperature. The desired product precipitates out and is rinsed with acetone, to give 5.5 g 4,5,6,7-tetrahydro-thieno[3,2-c]-pyridine hydrochloride (M.p=225° C.; Yield: 31%).

EXAMPLE 7

Preparation of 5-(2-chloro-benzyl)-4,5,6,7-tetrahydrothieno[3,2-c]pyridine hydrochloride (a) Preparation of chloromethylmethylthioether Into a 1 liter capacity three-necked flask are added 274 g (2.3 M) thionyl chloride and 400 ml methylene chloride. The mixture is refluxed (41° C.) and 156 g dimethylsulfoxide is slowly added thereto. A substantial gas evolvement is noted throughout the addition: it consists of $SO_2$ and HCl. Slight heating must be maintained to keep the medium under refluxing conditions. On completion of the dimethylsulfoxide addition, a nitrogen stream is bubbled through to remove the dissolved hydrochloric acid. The reaction medium (333 g) is used as such in the cyclization step described below. Gas phase chromatographic quantitative determination gives the following results:
-chloromethylmethylthioether : 56.77%
-methylene chloride :33%

(b) 5-(2-chloro-benzyl)-4,5,6,7-tetrahydro-thieno[3,2-c]pyridine hydrochloride

To 52 g (0.2 M) N-(2-chloro-benzyl)-2-(2-thienyl)ethylamine dissolved in 60 ml dimethylsulfoxide and heated at 60° C. are added, over 30 minutes, 51 g (0.3 M) crude chloromethylmethylthioether prepared in step (a) above. The temperature of the reaction medium increases gradually and it is maintained at 80°–85° C, throughout the addition step, by cooling with water. When addition of chloromethyl methylthioether is completed, the medium is cooled to 6° C. The desired product precipitates out readily. After filtration and washing with 2×70 ml acetone, there are obtained 44.1 g 5-(2-chloro-benzyl)-4,5,6,7-tetrahydro-thieno[3,2-c]pyridine hydrochloride (Yield: 73.5%). Treatment of the filtrates provides another 10 g of the desired product (Yield: 90% M.p.=190° C.). The resulting crude product contains 1-2% impurities and may be made analytically pure by recrystallization from ethanol.

EXAMPLE 8

Preparation of 5-(2-chloro-benzyl)-4,5,6,7-tetrahydrothieno[3,2-c]pyridine hydrochloride The same compound as in Example 1 is prepared in the following manner:

66.5 g (0.44 M) chloromethyl pivalate is reacted by heating, for 3 hours, with a solution of 103 g (0.4 M) N-(2-chloro-benzyl)-2-(2-thienyl)ethylamine in 300 ml dimethylsulfoxide, to give the title compound in a yield of 51%.

EXAMPLE 9

Preparation of 5-(2-chloro-benzyl)-4,5,6,7-tetrahydrothieno[3,2-c]pyridine hydrochloride To 42 ml dimethylformamide in which are dissolved 0.25 mole gaseous hydrochloric acid and heated at 40° C. is added, over 2 minutes, a mixture of 25.15 g (0.1 M) N-(2-chloro-benzyl)-2-(2-thienyl)ethylamine and 15.3 g (0.033 M) s.hexahydrotriazine of o.chlorobenzylamine. The reaction is exothermal and, during the addition, the reaction must be cooled with water to maintain the temperature of the reaction medium below 70° C. After completion of the addition, stirring is continued for a further 30 minutes and the material is then cooled. The desired product is filtered off and washed twice with acetone, to give 17.3 g 5-(2-chloro-benzyl)-4,5,6,7-tetrahydro-thieno[3,2-c]pyridine hydrochloride. Treatment of the filtrates provides another 20 g of the desired product (Overall yield: 90%).

EXAMPLES 10–12

Preparation of 5-(2-chloro-benzyl)-4,5,6,7-tetrahydrothieno[3,2-c]pyridine hydrochloride Using the same procedure as described in Example 9, the title compound is obtained by substituting s.hexahydrotriazine of o.chlorobenzylamine with:
 -s.hexahydrotriazine of n.butylamine (yield ≃ 90%)
 -urotropine (yield: 60%)
 -paraformaldehyde (yield: 83%).

EXAMPLE 13

Preparation of 4,5,6,7-tetrahydro-thieno[3,2-c]pyridine hydrochloride

To 73 ml dimethylformamide heated at 45° C. in which are dissolved 0.45 mole gaseous hydrochloric acid, is added, over 25 minutes, a mixture of 17 g (0.2 M) s.hexahydrotriazine of n. n.butylamine/and 26 g 2-(2-thienyl)ethylamine. The temperature of the medium is maintained at 45° C. throughout the addition by means of a cold water bath. The desired product precipitates out at the end of the addition. Filtration gives 22.16 g 4,5,6,7-tetrahydrothieno[3,2-c]pyridine hydrochloride (Yield: 65%).

EXAMPLE 14

Preparation of 5-(2-chloro-benzyl)-4,5,6,7-tetrahydrothieno[3,2-c]pyridine hydrochloride To 2.25 g (0.075 M) paraformaldehyde suspended in 20 ml dimethylformamide are added 9.61 g (0.1 M) methanesulfonic acid. The medium being at a temperature of 72° C., 13 g (0.05 M) N-(2-chloro-benzyl)-2-(2-thienyl)ethylamine dissolved in 5 ml dimethylformamide are added over 2 minutes. The temperature of the reaction medium reaches 90° C. The reaction medium is then cooled to 20° C. and poured over 50 ml 4N sodium hydroxide. The material is extracted with 1×30 ml and then 1×20 ml methylene chloride. The organic phases are combined, dried over sodium sulfate and evaporated, to give an oil which is taken up into 30 ml ethanol in which are dissolved 0.15 mole gaseous hydrochloric acid. After partial evaporation of the ethanol, the desired product precipitates out. It is filtered, washed with acetone and dried, to give 11.35 g 5-(2-chloro-benzyl)-4,5,6,7-tetrahydrothieno[3,2-c]pyridine hydrochloride (Yield: 75.6%).

Having now described our invention what we claim as new and desire to secure by Letters Patent is:

1. Process for the preparation of compounds having the general formula:

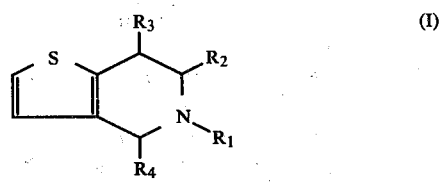

in which $R_1$ is a member selected from the group consisting of $C_{1-7}$ alkyl; phenyl lower alkylene, phenyl lower alkylene in which the phenyl is substituted with 1 to 3 substituents selected from the group consisting of lower alkyl, hydroxy, lower acyloxy, lower alkoxy, nitro and halogen; naphthyl lower alkylene; thienyl lower alkylene; diphenyl lower alkylene; phenyl hydroxy-lower-alkylene; phenyl hydroxy-lower-alkylene in which the phenyl is substituted with 1 to 3 substituents selected from the group consisting of lower alkyl, hydroxy, lower acyloxy, lower alkoxy, nitro and halogen; naphthyl hydroxy-lower-alkylene; thienyl hydroxy-lower-alkylene; and diphenyl hydroxy-lower-alkylene; $R_2$ is selected from the group consisting of hydrogen and lower alkyl; $R_3$ is hydrogen; and $R_4$ is hydrogen, comprising reacting a compound having the formula:

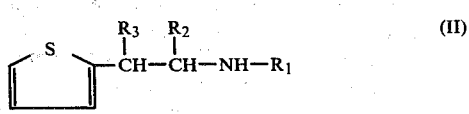

in which $R_1$, $R_2$ and $R_3$ are as defined above, with a compound having the formula:

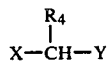

in which $R_4$ is as defined above; X is a radical selected from the group consisting of halogen, amino and substituted amino; and Y represents a radical selected from the group consisting of lower alkoxy, substituted lower alkoxy, thio(lower)alkyl, substituted thio(lower)alkyl, amino, substituted amino, and a group of the formula:

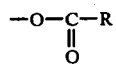

in which R is a radical selected from lower alkyl, or both the groups X and Y, together with the carbon atom to which they are attached, form a 6-membered nucleus selected from hexahydro-S—triazinic and trioxannic heterocyclic nucleus, in an inert solvent, at a temperature between 0° and 150° C. and in an anhydrous medium.

2. Process as claimed in claim 1, and thereafter liberating the free base.

3. Process as claimed in claim 1, wherein said inert solvent is a polar aprotic solvent such as dimethylformamdide, dimethylsulfoxide, hexamethylphosphorotriamide, or benzene or a chlorinated solvent such as a chlorinated hydrocarbon or a light ether.

4. Process as claimed in claim 3, wherein the solvent contains an inorganic or organic acid of carboxylic or sulfonic type.

5. Process as claimed in claim 4, wherein said acid is hydrochloric acid or methane sulfonic acid.

6. Process as claimed in claim 3, wherein the solvent is selected so as to be a non-solvent for the halide of the compound of the formula (I).

7. Process as claimed in claim 1, wherein the compound of the formula (III) is reacted in an amount comprised between the stoichiometric amount and a molar excess of 50% with respect to the compound of the formula (II).

* * * * *